United States Patent
Brown et al.

(10) Patent No.: US 10,525,210 B2
(45) Date of Patent: Jan. 7, 2020

(54) MODULE FOR A SHARPS RETRACTION DEVICE

(71) Applicant: C-MAJOR LTD., Buckinghamshire (GB)

(72) Inventors: Philip Brown, Lancashire (GB); Allen Pearson, Cambridgeshire (GB); James Collins, Cambridgeshire (GB)

(73) Assignee: C-MAJOR LTD. (GB)

( * ) Notice: Subject to any disclaimer, the term of this patent is extended or adjusted under 35 U.S.C. 154(b) by 147 days.

(21) Appl. No.: 15/738,256

(22) PCT Filed: Jun. 7, 2016

(86) PCT No.: PCT/GB2016/051674
§ 371 (c)(1),
(2) Date: Dec. 20, 2017

(87) PCT Pub. No.: WO2016/207605
PCT Pub. Date: Dec. 29, 2016

(65) Prior Publication Data
US 2018/0193570 A1   Jul. 12, 2018

(30) Foreign Application Priority Data
Jun. 22, 2015   (GB) .................................. 1510943.2

(51) Int. Cl.
*A61M 5/32*   (2006.01)
*A61M 5/34*   (2006.01)

(52) U.S. Cl.
CPC .......... *A61M 5/345* (2013.01); *A61M 5/3221* (2013.01); *A61M 5/3232* (2013.01); *A61M 2005/3227* (2013.01)

(58) Field of Classification Search
CPC ........ A61M 2005/3227; A61M 5/3221; A61M 5/3232; A61M 5/345; A61M 5/31596;
(Continued)

(56) References Cited

U.S. PATENT DOCUMENTS 5,498,245 A * 3/1996 Whisson ............... A61M 5/322
128/919
5,728,073 A * 3/1998 Whisson ............... A61M 5/322
604/194

(Continued)

FOREIGN PATENT DOCUMENTS

GB        2453365 A    4/2009
GB        2497305 A    6/2013
(Continued)

OTHER PUBLICATIONS

PCT International Search Report, dated Aug. 29, 2016, PCT/GB2016/051674.
(Continued)

*Primary Examiner* — Rebecca E Eisenberg
(74) *Attorney, Agent, or Firm* — Luedeka Neely Group, PC

(57) ABSTRACT

A fluid extraction device is provided for extracting fluid from a syringe assembly including a syringe port and a sleeve. The device includes a body with first and second ends, the first end defining a fluid entry port, and the second end defining a fluid exit port. A channel through the body connects the fluid entry and fluid exit ports. At least one push member extends radially from the body and is configured to contact the sleeve of the syringe assembly in use such to push it from a first position in which the sleeve closes the syringe port to a second position in which the sleeve exposes the syringe port.

16 Claims, 7 Drawing Sheets

(58) Field of Classification Search
CPC .. A61M 5/2066; A61M 5/24; A61M 5/31581; A61J 1/22
See application file for complete search history.

(56) References Cited

U.S. PATENT DOCUMENTS

| | | | | |
|---|---|---|---|---|
| 2002/0068907 | A1* | 6/2002 | Dysarz | A61M 5/3232 604/191 |
| 2004/0204688 | A1* | 10/2004 | Lin | A61M 5/3232 604/192 |
| 2004/0225274 | A1 | 11/2004 | Jansen et al. | |
| 2011/0083489 | A1* | 4/2011 | Glunz | G01M 3/3236 73/1.79 |
| 2012/0078225 | A1* | 3/2012 | Zivkovic | A61M 5/3213 604/506 |
| 2015/0374916 | A1* | 12/2015 | Bertolote | A61M 5/19 604/82 |

FOREIGN PATENT DOCUMENTS

| | | |
|---|---|---|
| WO | 2008093063 A2 | 8/2008 |
| WO | 2013083979 A1 | 6/2013 |

OTHER PUBLICATIONS

IP Office, Priority Application Search Report, dated Dec. 21, 2015, GB 510943.2 Patents Act 1977—Search Report under Section 17.

* cited by examiner

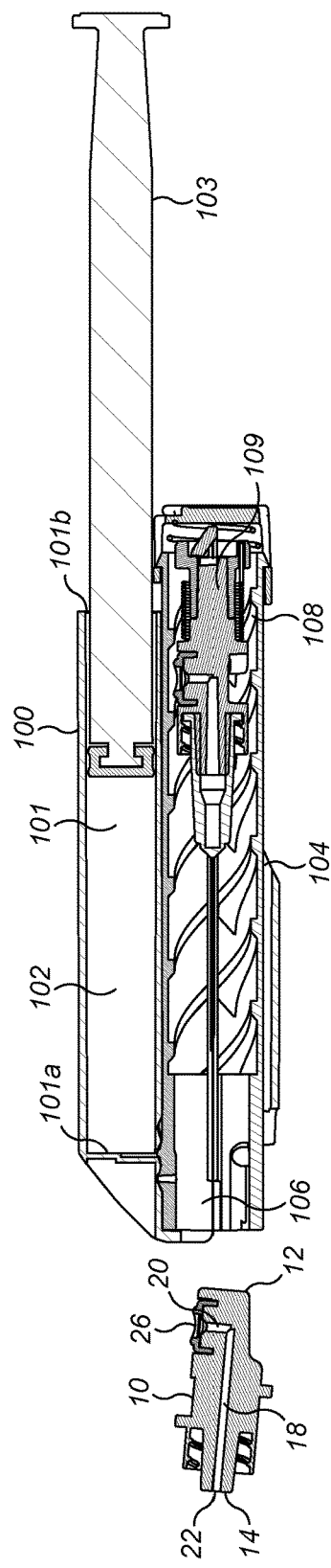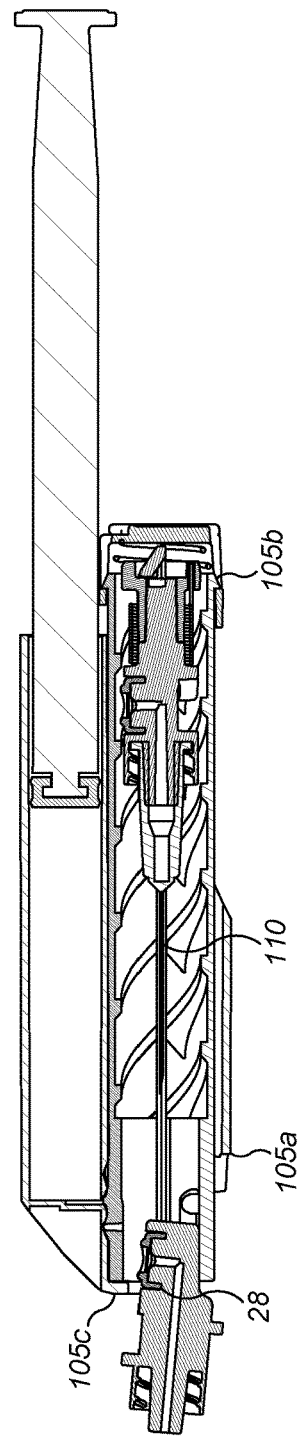
FIG. 2A
FIG. 2B

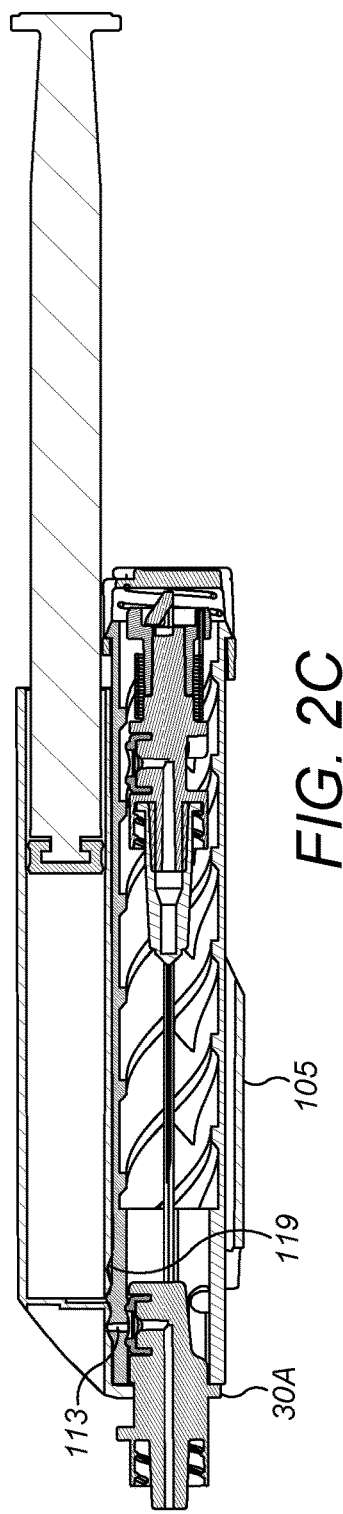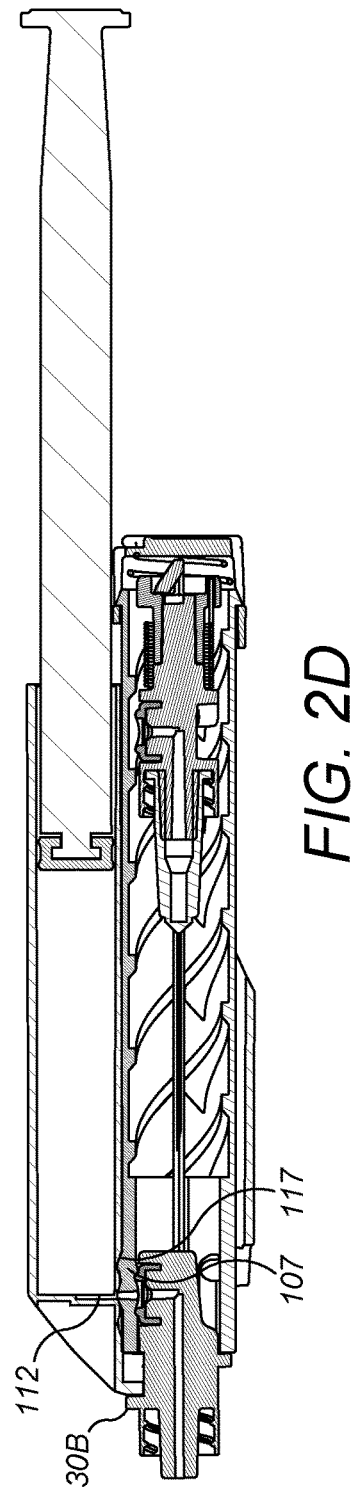

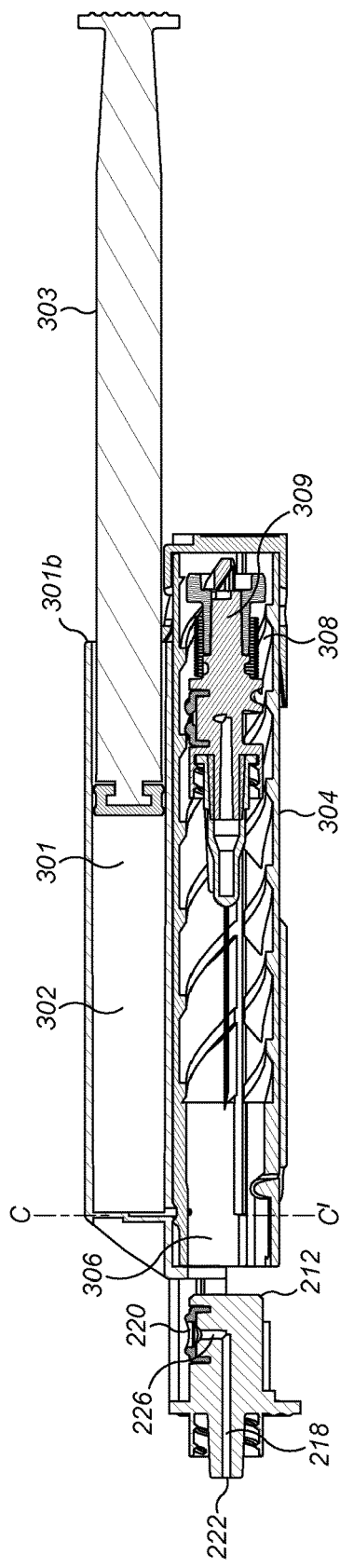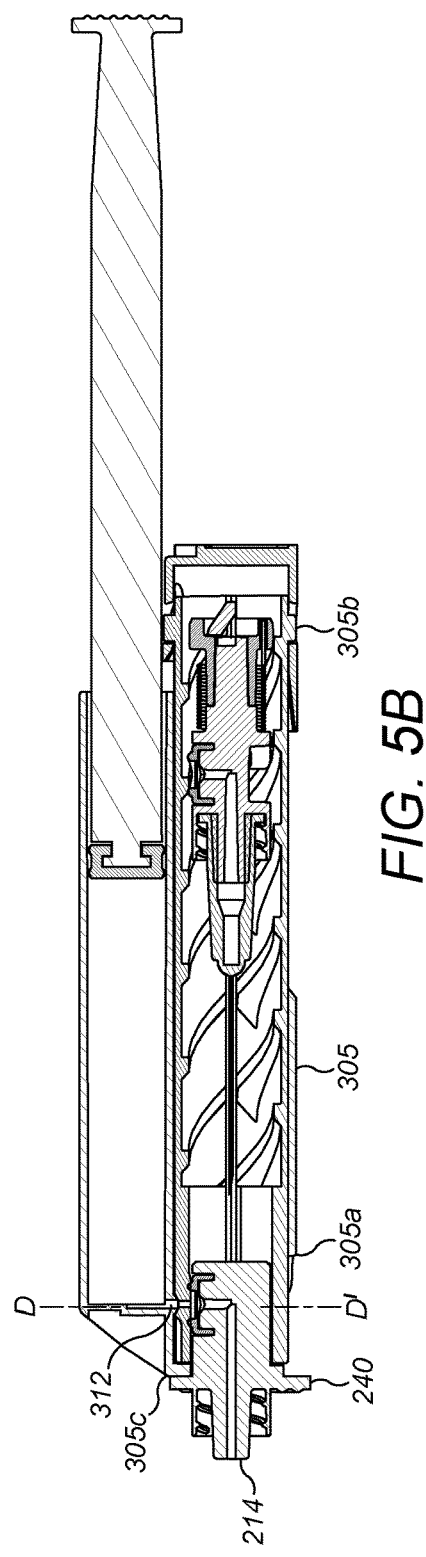
FIG. 5A
FIG. 5B

MODULE FOR A SHARPS RETRACTION DEVICE

CROSS-REFERENCE TO RELATED APPLICATION

This application claims priority under all applicable statutes, and is a U.S. National phase (37 U.S.C. Section 371) of International Application PCT/GB2016/051674, filed Jun. 7, 2016, and entitled A MODULE FOR A SHARPS RETRACTION DEVICE, which claims priority to GB 1510943.2, filed Jun. 22, 2015, incorporated herein by reference in their entireties.

The present invention relates to a device for removing fluid from a medical syringe assembly.

The term "sharps" is well known in the medical field, and is used herein, to mean needles and any other instruments with points, blades, cutting edges etc. which are potentially hazardous.

In WO2013/083979, there are disclosed two embodiments of syringe assembly. Both assemblies provide means for isolating a medical sharp after it has been used to minimise subsequent injury or infection.

The second of these two embodiments from WO2013/083979, i.e. the embodiment shown in FIGS. 7-10 from the document, is particularly suited for aspirating fluid from a patient. In this embodiment, after the fluid has been aspirated and the sharp has been retracted, the fluid that has been aspirated is contained inside a reservoir of fluid inside the syringe assembly. There is therefore the need to be able to quickly and easily remove this fluid from the assembly, and also other assemblies with a similar design.

Accordingly, there is provided a fluid extraction device for extracting fluid from a syringe assembly of the type comprising:

a housing defining a fluid chamber, a plunger reciprocable in the chamber, a syringe port in the housing for fluid to enter and exit the chamber and a slidable sleeve movable between a first position in which the sleeve closes the syringe port and a second position in which the sleeve exposes the syringe port;

wherein the fluid extraction device comprises a body with first and second ends, the first end defining a fluid entry port, the second end defining a fluid exit port, a channel through the body connecting the fluid entry and fluid exit ports, at least one push member extending radially from the body and configured to contact the sleeve of the syringe assembly in use and to push it from the first position to the second position, at least one stop member on the body and configured to contact the housing of the syringe assembly when the push member has moved the sleeve to the second position, thereby bringing the fluid entry port into fluid communication with the syringe port, and a connector at the second end of the body for releasably connecting a fluid collection container.

The fluid extraction device thus allows fluid from the syringe assembly to be easily and conveniently transferred without spillage of the fluid.

The body may be substantially cylindrical, with a longitudinal axis, a circumferential surface and first and second end faces, and wherein the fluid entry port and fluid exit port are not axially aligned with each other.

In this case, the fluid entry port may be in the circumferential surface of the body and the fluid exit port may be in the second end face of the body. Locating the ports on the body in this way makes the device particularly suited for use with the second embodiment of syringe assembly disclosed in WO2013/083979.

The push member may comprise a collar extending partially round the circumference of the body. This allows the push member to more conveniently push the sleeve to its second position.

The stop member may project radially from the body.

The stop member may comprise a collar extending partially around the circumference of the body.

The at least one push member and at least one stop member may be axially spaced from one another. In this case, the stop member may be located axially between the push member and the second end of the body.

The push member and the stop member may be joined by a pair of axially extending ribs.

The push member may be wedge shaped. The wedge preferably extends in an axial direction along the outer surface of the body. The thin end of the wedge is preferably located toward the second end of the device, whilst the larger end of the wedge is located towards the first end of the device.

The stop member preferably comprises at least one guide rail to help guide the device onto any syringe assembly that requires fluid removal therefrom.

The connector may comprise one of a screw thread, a push-fit connector or a twist-lock connector. Use of these specific types of connector allows the device to be more readily used with standard fluid collection containers.

The fluid extraction device may further comprise a valve in the fluid entry port configured to open if fluid pressure external to the device exceeds fluid pressure internal to the device. With such a valve, the device will only receive fluid from the fluid chamber when the plunger from the syringe assembly is depressed. Therefore the presence of this valve allows the removal of fluid from the syringe assembly to be better controlled.

The fluid extraction device may further comprise an O-ring seal surrounding the fluid entry port to minimise fluid leakage at the interface between the fluid entry port and the syringe port.

The present invention also provides a combination of a fluid extraction device as set out in the claims with a syringe assembly of the type set out in claim 1. By providing the two components together, this allows the user to conveniently aspirate fluid from a patient using the syringe assembly, and then quickly remove the aspirated fluid from the syringe assembly using the fluid extraction device.

In this case, the fluid extraction device and the syringe assembly may be provided sealed in a sterile package. This helps to keep the syringe assembly and fluid extraction device sterile right up to the point of use.

The invention will now be described with reference to the accompanying drawings in which:

FIGS. 2A-2D show cross section views of the first device according to the present invention, at different stages of its operation, being used on a first type of syringe assembly.

FIG. 4A shows the second fluid extraction device in a non-deployed position, whilst FIG. 4B shows the device in a deployed position.

FIGS. 5A and 5B show cross section views of the second fluid extraction device being used on a second type of syringe assembly. FIG. 5A shows the second fluid extraction device in the non-deployed position, whilst FIG. 5B shows the device in the deployed position.

Figure 1A:
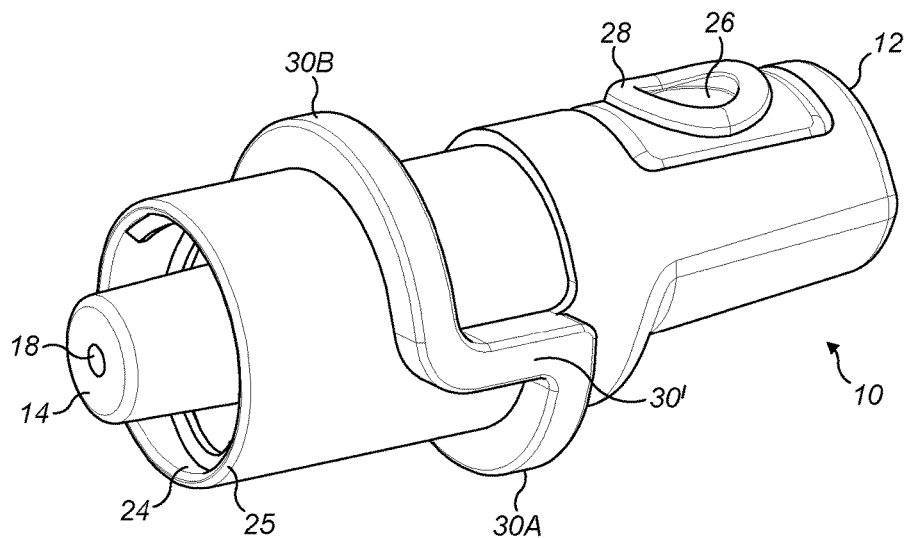
FIGS. 1A and 1B show perspective views from opposite ends of a first fluid extraction device of the present invention.
Figure 1B:
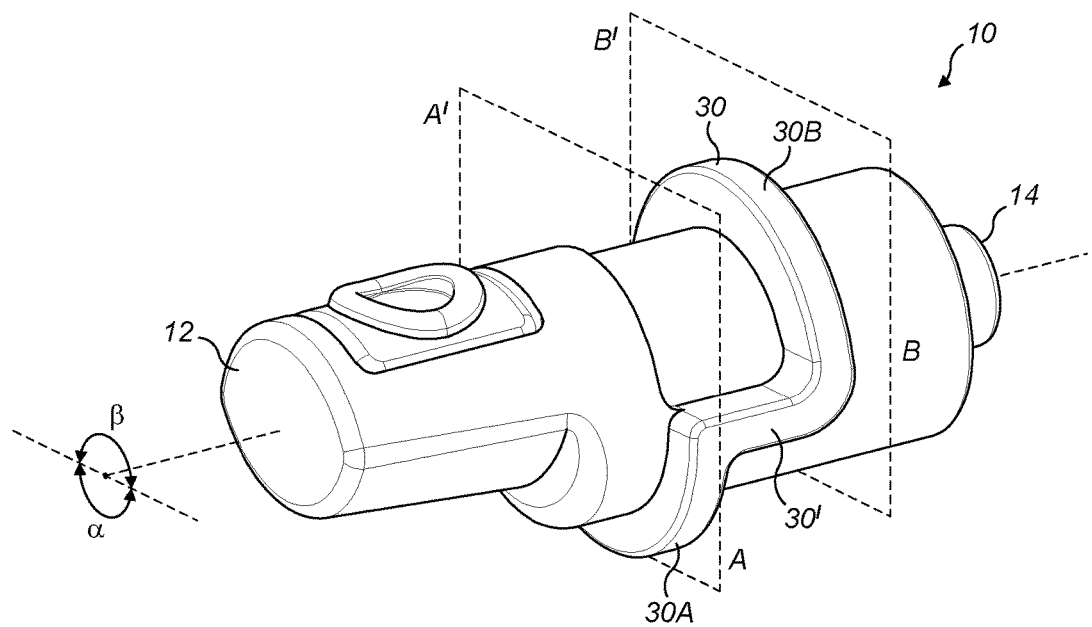

A first device according to the present invention is shown best with reference to FIGS. 1A and 1B. The device 10 is formed of an 'eye' shaped cylindrical component comprising a proximal end 12 and a distal end 14. The eye shaped component is generally cylindrical about a longitudinal axis and has a proximal end 12 with an elliptical cross section, wherein the elongate ends of this elliptical cross section are pointed.

Extending through the device 10 is a passage for fluid 18 (best seen in FIG. 2A). The passage for fluid 18 comprises a first port 20 in a proximal portion of the circumferential surface of the device 10, and comprises a second port 22 which is exposed at the distal end 14 of the device 10. The passage 18 has a circular cross section and is generally L-shaped. In use, fluid is able to pass into the passage from the first port 20 on the circumferential surface of the device, through the passage, and out from the passage via the second port 22 located at the distal end of the device 10.

The distal end 14 of the device 10 is shaped to be connected to a separate container for fluid (not shown). In particular, the distal end 14 may be shaped in the form of a connector 24 for allowing the device 10 to be connected to other standard medical containers. In FIGS. 1A and 1B, the connector 24 is shown as a screw thread which extends around the inside surface of a tubular portion 25 which is coaxially located around the second port 22. This screw thread is then connectable with a screw top from a container for fluid (not shown). The connector 24 could alternatively be a push-fit or a twist-lock type connector. The connector 24 may also be a conventional LuerLock connector.

A valve 26 is attached to the device 10 and closes the first port 20 when the device 10 is not in use as will be described. The valve may for example be a resilient diaphragm with a slit which is closed in a rest state. The slit will open only if pressure on the outer side of the valve 26 is increased.

Surrounding the first port 20 on the circumferential surface of the device 10 is an o-ring seal 28 to prevent fluid leakage when the device is used as will be described.

The device 10 includes a radial protrusion, in this example in the form a collar 30 which extends around the circumferential surface of the device. The collar 30 is stepped so that a first portion 30A extends around a first cross section A-A' of the device and about a first angular portion a, whilst a second portion 30B extends around a second cross section of the device B-B' and at a different angular portion 13. A pair of axially extending ribs 30' connects the first and second portions 30A; 30B of the collar 30 together.

A separate collar could be used for each of portions 30A and 30B. Each portion of the collar could also be formed of one or more separable radial protrusions instead of one continuous radial protrusion.

The device 10 could be used with a syringe assembly of the type disclosed in WO2013/083979, in particular the embodiment shown in FIGS. 7-10 from that document. The device is also intended to be used with other syringe assemblies of similar design.

An example of a suitable syringe assembly 100 is shown in FIGS. 2A-2D.

The syringe assembly 100 is formed by a housing which forms two channels which are substantially parallel with one another.

The first channel is formed within a first tubular wall 101 which comprises a distal end wall 101a and an open proximal end 101b. A plunger 103 is insertable in the open proximal end 101b such that it can slide within the tubular wall 101. Together, the plunger 103, the tubular wall 101 and the distal end wall 101a define a reservoir for fluid 102, whose size is controlled depending on the position of the plunger 103.

The second channel is located next to the first channel and is formed by a second tubular wall 105 comprising an open distal end 105a and an open proximal end 105b. A portion of this open distal end 105a comprises a lip 105c which extends radially inwardly a short distance from the second tubular wall 105. Within the second tubular wall 105 is a tubular sleeve 104 comprising a distal end 106 and a proximal end 108. The tubular sleeve 104 can slide axially in relation to the second tubular wall 105 but cannot rotate inside it. Such rotation is prevented by a row of axially spaced protrusions 117 which are located on the outer surface of the tubular sleeve 104 and which are operable to engage with a corresponding set of recesses 119 located on the inner surface of the second tubular wall 105.

The interior of the tubular sleeve 104 contains a sharp sub-assembly 109 for holding a medical sharp 110, in particular a needle. The sub-assembly is moveable from an unretracted state whereby the medical sharp 110 projects from the distal end 106 of the tubular sleeve 104 to aspirate or dispense fluid into a patient. The syringe assembly 100 also comprises a retraction means for both manually and automatically retracting the sub-assembly 109 toward the proximal end 108 of the tubular sleeve 104, after use of the medical sharp 110, which causes the medical sharp 110 to be retracted inside the tubular sleeve 104.

A syringe port 112 is located in the syringe assembly 100 to provide a passage for fluid between the reservoir 102 and the interior of the second tubular wall 105. The syringe port 112 is formed in the distal end wall 101a and extends through the first tubular wall 101 and into the second channel defined by the second tubular wall 105.

A fluid port 113 is located in a distal portion of the tubular sleeve 104. Both the fluid port 113 and the syringe port 112 are located at the same circumferential position on the syringe assembly (and are fixed in these circumferential positions by the protrusions 117 and recesses 119). In the unretracted state of the assembly 100, the fluid port 113 and the syringe port 114 connect with the medical sharp 110 from the assembly 100 to allow fluid to be injected into, and aspirated from, the patient.

In its retracted state, the medical sharp 110 is retracted to the proximal end 108 of the sleeve 104. In this position (see FIG. 2A), the sleeve 104 is in a distalmost position inside the second tubular wall 105. In this position, the syringe port 112 is axially offset with the fluid port 113.

From the assembly's retracted state, the sleeve 104 is movable inside the second tubular wall 105 in a proximal direction to a dispensing position as shown in FIG. 2D in which the fluid port 113 is aligned with the syringe port 112. Movement of the sleeve 104 from its retracted state to its dispensing position is done using the fluid extraction device 10 of the present invention, as will now be described with reference to FIGS. 2A-2D.

Initially, the proximal end 12 of the fluid extraction device 10 is inserted into the open distal end 105a of the second tubular wall 105. The device 10 is sized so that the first portion 30A of the collar 30 abuts the distal end of the sleeve 104 (see FIG. 2C). Once in this position, the first port 20 is aligned with the fluid port 113 which is located on the sleeve 104.

From this position (see FIG. 2C), by pushing the device 10 in a proximal direction relative to the syringe assembly 100 the first portion 30A of the collar 30 applies pressure on the tubular sleeve 104.

Once enough pressure is applied, each protrusion 117 from the tubular sleeve 104 will be forced from its initial position in one of the recesses 119 in a proximal direction into a neighbouring recess 119 in the second tubular wall 105. In this position, the second portion 30B of the collar 30 abuts the lip 105c of the second tubular wall 105, thus preventing the device 10 from being pushed any further inside the syringe assembly (see FIG. 2D).

From this position as shown in FIG. 2D, the first port 20 from the device 10, the fluid port 113 from the tubular sleeve 105, and the syringe port 112 are all aligned to form a path for fluid to escape from the reservoir 102. However, the valve 26 on the device 10 which blocks the first port 20 prevents this fluid from entering the device 10.

By depressing the plunger 103 to reduce the size of the reservoir 102, an increased fluid pressure is exerted on the valve 26 of the device 10 which causes the valve to open, thus allowing fluid to flow through the first port 20 into the passage 18 in the device 10 and out from the second port 22 into any container (not shown) connected to the device 10 via the connector 22. During this fluid transfer, the o-ring seal 28 from the device 10, which surrounds the interface between the fluid port 113 on the tubular sleeve 105 and the first port 20 on the device 10, prevents any fluid from leaking around the device 10 and into the tubular sleeve 105.

It will be appreciated that a number of variations and modifications can be made to the invention without departing from the scope of the claims.

For instance, it will appreciated that the tubular sleeve 104 could be twisted between a first angular position and a second angular position relative to, rather than moved from a first axial position to a second axial position inside, the second tubular wall 105. In this case, the protrusions 117 and recesses 119 could be located in different circumferential positions rather than different axial positions on the respective tubular sleeve 104 and second tubular wall 105. In this case, a portion of the collar 30 from the device 10 would engage with a corresponding portion in the tubular sleeve 104 to allow the device to grip and rotate the sleeve 104.

An example of such a twist type mechanism is shown in FIGS. 3A-6B. Disclosed in these Figures is a second device 210 according to the present invention, and a syringe assembly 300 for use with this device 210.

Figure 3A:
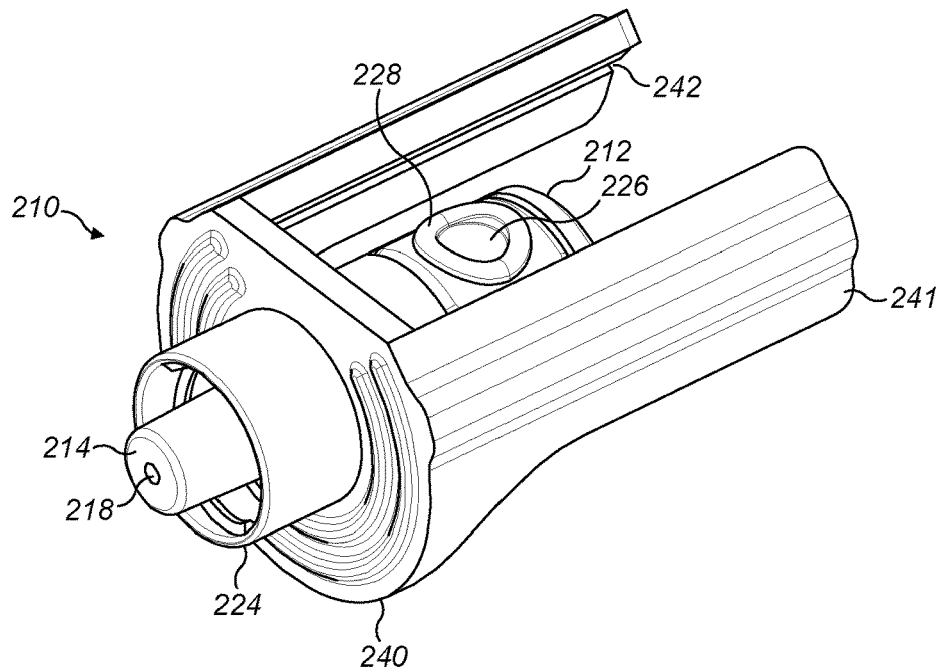
FIGS. 3A and 3B show respective top and bottom perspective views of a second fluid extraction device of the present invention.
Figure 3B:
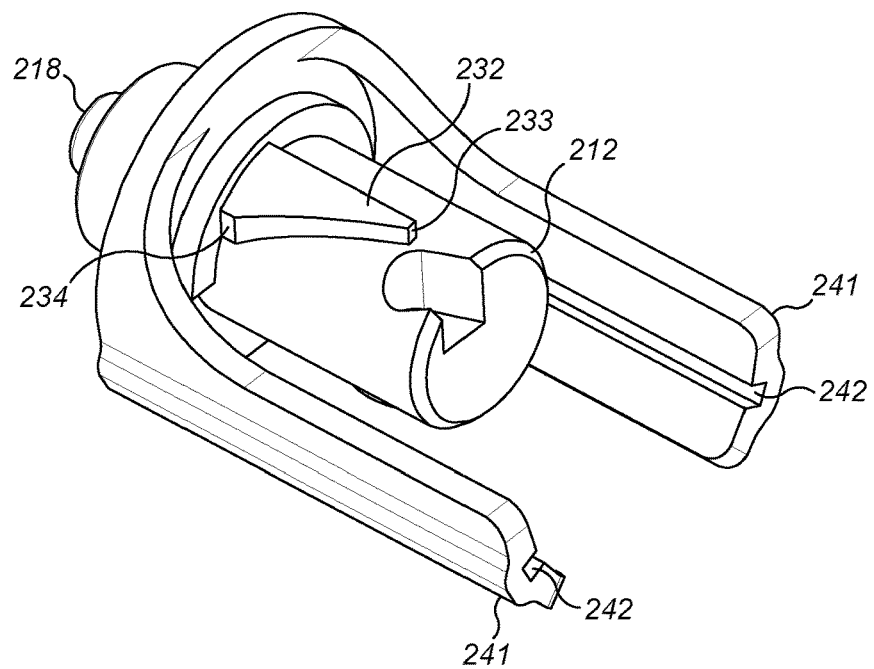

The second device 210 is shown best with reference to FIGS. 3A and 3B. Where features are common to the first device 10 and the second device 210, corresponding reference numerals are used (e.g. 10 corresponds to 210, 22 corresponds to 222, and 26 corresponds to 226).

As with the first device 10, the second device 210 is formed of a generally cylindrical component comprising a main body 211 defining a proximal end 212 and a distal end 214. The component is generally cylindrical about a longitudinal axis and has a proximal end 212 with a circular cross section.

Extending through the device 210 is a passage for fluid 218 (best seen in FIG. 5A). The passage for fluid 218 comprises a first port 220 in a proximal portion of the circumferential surface of the device 210, and comprises a second port 222 which is exposed at the distal end 214 of the device 210. The passage 218 has a circular cross section and is generally L-shaped. In use, fluid is able to pass into the passage from the first port 220 on the circumferential surface of the device, through the passage, and out from the passage via the second port 222 located at the distal end of the device 210.

The distal end 214 of the device 210 is shaped to be connected to a separate container for fluid (not shown) via a connector 224 (which is identical to the connector 24 described in relation to the first device 10).

A valve 226, identical to the valve 26, is attached to the device 210 and closes the first port 220 when the device 210 is not in use. Surrounding the first port 220 on the circumferential surface of the device 210 is an o-ring seal 228 to prevent fluid leakage when the device is used.

A radial projection in the shape of a wedge 232 extends in an axial direction along the outer surface of the body 211. The wedge 232 is located on the opposite side of the body 211 to that of the port 220. The thin end 233 of the wedge is located toward the proximal end 212 of the device 210, whilst the larger end 234 of the wedge 232 is located towards the distal end 214 of the device.

The device 210 includes an outwardly extending radial protrusion 240 toward the distal end 214 of the device 210. Two legs 241 axially extend in a proximal direction from the radial protrusion 240. Each leg is radially spaced from the outer surface of the 'eye' shaped cylindrical body 211, and comprises a straight guide slot 242 extending along the length of the leg's inner surface.

The device 210 could be used with a syringe assembly 300 of the type disclosed in FIGS. 4A-6B. Syringe assembly 300 is a variant of the syringe assembly 100 shown in FIGS. 2A-2D. Corresponding reference numerals are used to show features common to the two syringe assemblies (e.g. 100 corresponds to 300, and 105 corresponds to 305).

The syringe assembly 300 is formed by a housing which forms two channels which are substantially parallel with one another.

The first channel is formed within a first tubular wall 301 which comprises a distal end wall 301a and an open proximal end 301b. A plunger 303 is insertable in the open proximal end 301b such that it can slide within the tubular wall 301. Together, the plunger 303, the tubular wall 301 and the distal end wall 301a define a reservoir for fluid 302, whose size is controlled depending on the position of the plunger 303.

The second channel is located next to the first channel and is formed by a second tubular wall 305 comprising an open distal end 305a and an open proximal end 305b. A portion of this open distal end 305a comprises a lip 305c which extends radially inwardly a short distance from the second tubular wall 305. Within the second tubular wall 305 is a tubular sleeve 304 comprising a distal end 306 and a proximal end 308. In contrast to tubular sleeve 304 of the first syringe assembly 100, the tubular sleeve 304 of the second syringe assembly 300 can rotate in relation to the second tubular wall 305 but cannot axially slide inside it.

Figure 6B:
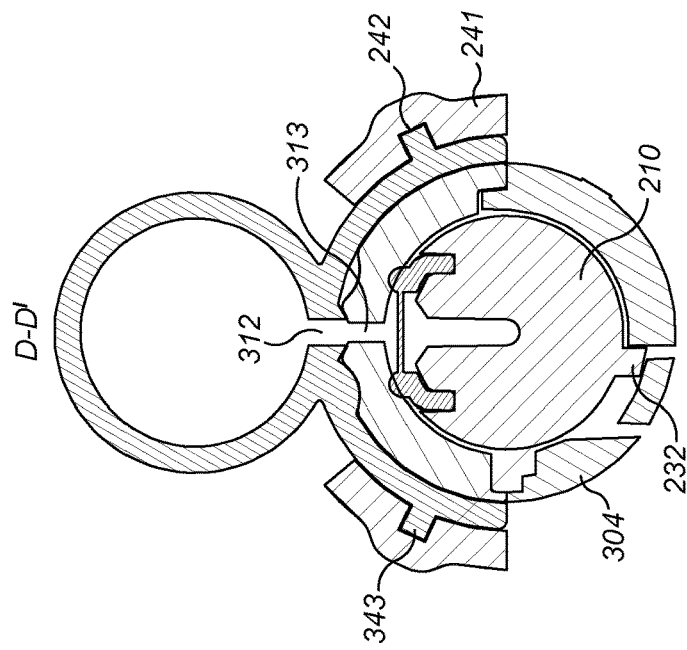
FIG. 6B is a cross section view showing the cross section D-D' shown in FIG. 5B.
Figure 6A:
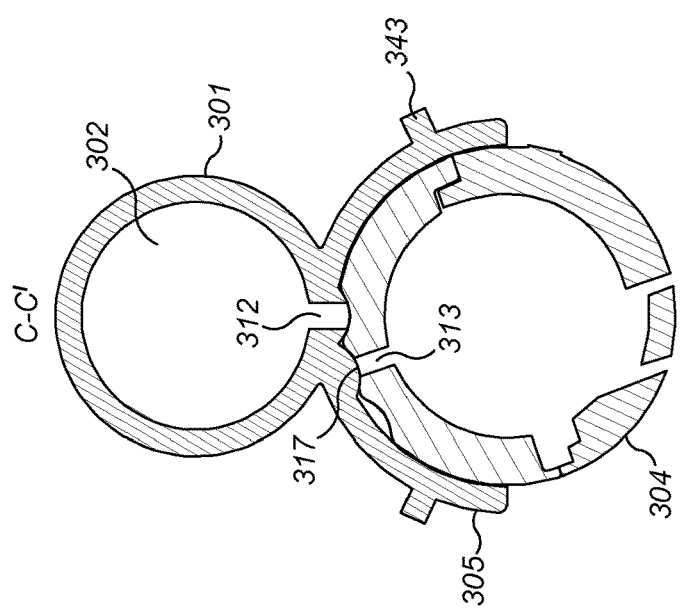
FIG. 6A is a cross section view showing the cross section C-C' shown in FIG. 5A.

Such axial movement is prevented by a row of axially aligned, but angularly spaced, protrusions 317 (as best shown in FIGS. 6A and 6B) which are located on the inner surface of the second tubular wall 305 and which are operable to engage with a corresponding set of recesses 319 located on the outer surface of the tubular sleeve 304.

As best shown in FIGS. 6A and 6B, a pair of straight guide rails 343 radially extends from the exterior surface of the second tubular wall 305. The rails 343 extend in an axial direction along the length of the wall 305, and are sized to fit within the two slots 242 located on the legs 241 of the device 210.

The interior of the tubular sleeve 304 contains a sharp sub-assembly 309 for holding a medical sharp 310, in particular a needle, as described previously in relation to sharp sub-assembly 109.

A syringe port 312 is located in the syringe assembly 300 to provide a passage for fluid between the reservoir 302 and the interior of the second tubular wall 305. The syringe port 312 is formed in the distal end wall 301a and extends through the first tubular wall 301 and into the second channel defined by the second tubular wall 305.

A fluid port 313 is located in a distal portion of the tubular sleeve 304. Both the fluid port 313 and the syringe port 312 are located at the same axial position on the syringe assembly (and are fixed in these axial positions by the protrusions 317 and recesses 319). In the unretracted state of the assembly 300, the fluid port 313 and the syringe port 314 connect with the medical sharp 310 from the assembly 300 to allow fluid to be injected into, and aspirated from, the patient.

In its retracted state, the medical sharp 310 is retracted to the proximal end 308 of the sleeve 304. In this position (see FIGS. 5A and 6A), the sleeve 304 is in a rotated position inside the second tubular wall 305. In this position, the syringe port 312 is angularly offset with the fluid port 313.

From the assembly's retracted state, the sleeve 304 is rotatable inside the second tubular wall 305 from a position as shown in FIG. 6A to a dispensing position as shown in FIG. 6B in which the fluid port 313 is aligned with the syringe port 312. Movement of the sleeve 304 from its retracted state to its dispensing position is done using the fluid extraction device 210 of the present invention, as will now be described.

Initially, the proximal end 212 of the fluid extraction device 210 is inserted into the open distal end 305a of the second tubular wall 305 by feeding the rails 343 of the syringe assembly 300 into the slots 242 from the device 210.

From this position (see FIGS. 4A, 5A and 6A), by pushing the device 210 in a proximal direction relative to the syringe assembly 300 the shape of the wedge 232 applies pressure on the tubular sleeve 304. The applied pressure increases as the device 210 is inserted into the syringe assembly due to the shape of the wedge 232.

Figure 4A:
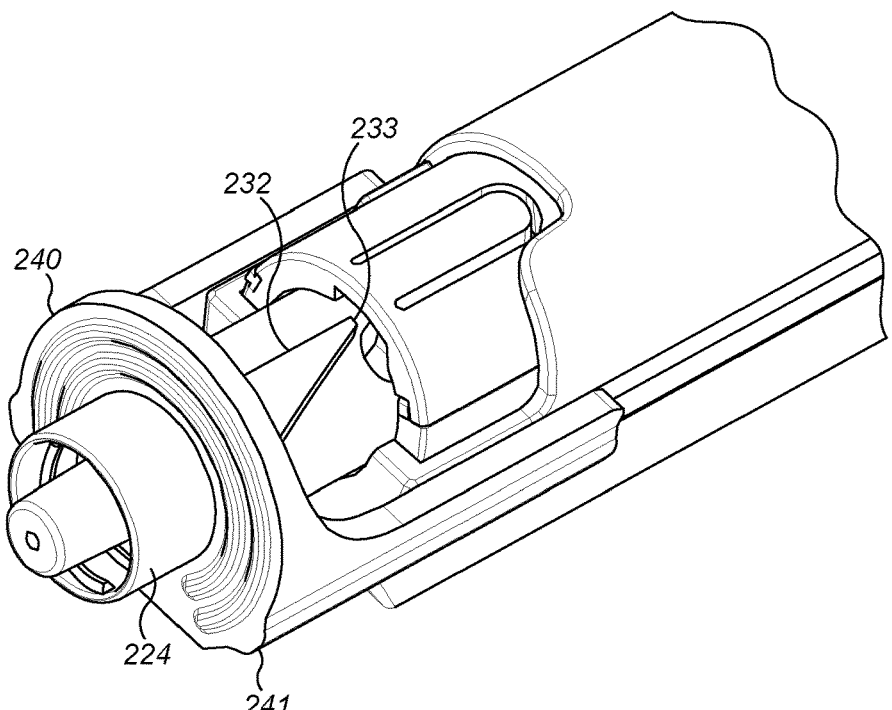
FIGS. 4A and 4B show bottom perspective views of the second fluid extraction device being used on a second type of syringe assembly.
Figure 4B:
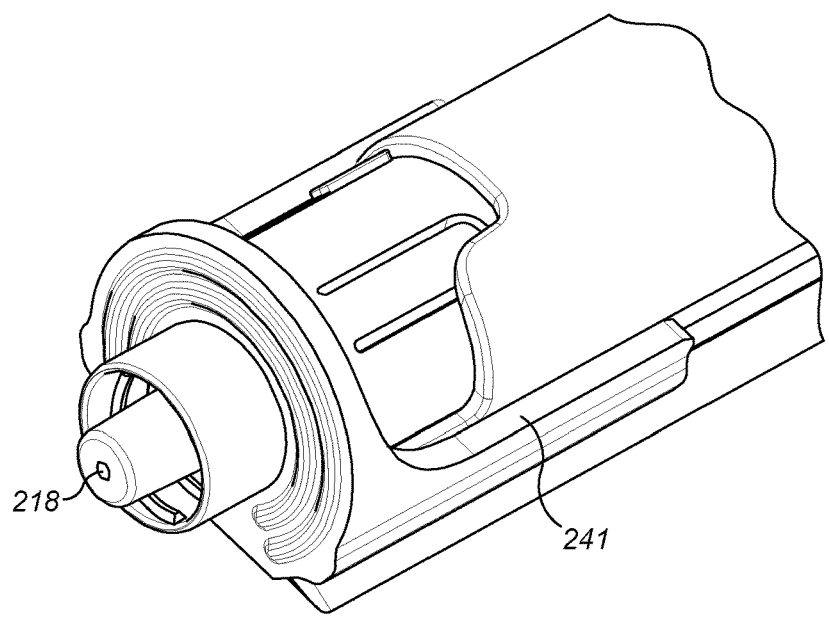

Once enough pressure is applied by the wedge 232, the recesses 317 and the tubular sleeve 304 are forced from their initial positions to rotate in relation to the protrusions 317 and the second tubular wall 305 to the dispensing position as shown in FIGS. 4B, 5B and 6B such that the fluid port 313 is aligned with the syringe port 312.

In the dispensing position, the first port 220 from the device 210, the fluid port 313 from the tubular sleeve 305, and the syringe port 312 are all aligned to form a path for fluid to escape from the reservoir 302. In this position, the radial protrusion 240 abuts the lip 305c of the second tubular wall 305, thus preventing the device 210 from being pushed any further inside the syringe assembly (see FIG. 6D).

It will be appreciated that the above devices could be provided in a sterile package before use. In this way, the devices can be kept sterile right up until the time they are intended to be used.

It will also be appreciated that the devices are not restricted to use in the medical field. Indeed, the devices are employable on any form of syringe assembly which contains fluid which requires removal therefrom.

Although the above devices have each been described with reference to a particular syringe assembly, the devices are intended to be be used with other configurations of syringe which have a fluid chamber, a port and a slideable member to open and close the port.

The invention claimed is:

1. A fluid extraction device for extracting fluid from a syringe assembly of the type comprising:
    a housing defining a fluid chamber, a plunger reciprocable in the chamber, a syringe port in the housing for fluid to enter and exit the chamber and a slidable sleeve movable between a first position in which the sleeve closes the syringe port and a second position in which the sleeve exposes the syringe port;
    wherein the fluid extraction device comprises a body with first and second ends, the first end defining a fluid entry port, the second end defining a fluid exit port, a channel through the body connecting the fluid entry and fluid exit ports, at least one push member extending radially from the body and configured to contact the sleeve of the syringe assembly in use and to push it from the first position to the second position, at least one stop member on the body and configured to contact the housing of the syringe assembly when the push member has moved the sleeve to the second position, thereby bringing the fluid entry port into fluid communication with the syringe port, and a connector at the second end of the body for releasably connecting a fluid collection container.

2. A fluid extraction device as claimed in claim 1, wherein the body is substantially cylindrical, with a longitudinal axis, a circumferential surface and first and second end faces, and wherein the fluid entry port and fluid exit port are not axially aligned with each other.

3. A fluid extraction device as claimed in claim 2, wherein the fluid entry port is in the circumferential surface of the body.

4. A fluid extraction device as claimed in claim 2, wherein the fluid exit port is in the second end face of the body.

5. A fluid extraction device as claimed in claim 1, wherein the push member comprises a collar extending partially round the circumference of the body.

6. A fluid extraction device as claimed in claim 1, wherein the stop member projects radially from the body.

7. A fluid extraction device as claimed in claim 1, wherein the stop member comprises a collar extending partially around the circumference of the body.

8. A fluid extraction device as claimed in claim 1, wherein the at least one push member and at least one stop member are axially spaced from one another.

9. A fluid extraction device as claimed in claim 8, wherein the stop member is located axially between the push member and the second end of the body.

10. A fluid extraction device as claimed in claim 8, wherein the push member and the stop member are joined by a pair of axially extending ribs.

11. A fluid extraction device as claimed in claim 1, wherein the push member is wedge shaped.

12. A fluid extraction device as claimed in claim 1, wherein the stop member comprises at least one guide rail.

13. A fluid extraction device as claimed in claim 1, wherein the connector comprises one of a screw thread, a push-fit connector or a twist-lock connector.

14. A fluid extraction device as claimed in claim 1, further comprising a valve in the fluid entry port configured to open if fluid pressure external to the device exceeds fluid pressure internal to the device.

15. A fluid extraction device as claimed in claim 1, further comprising an O-ring seal surrounding the fluid entry port.

16. A combination as set out in claim 1, wherein the fluid extraction device and the syringe assembly are sealed in a sterile package.

* * * * *